United States Patent [19]

Popli et al.

[11] Patent Number: 5,563,177
[45] Date of Patent: Oct. 8, 1996

[54] TASTE MASKING GUAIFENESIN CONTAINING LIQUIDS

[75] Inventors: Shankar D. Popli, Marlton; Zenaida O. Go, Hammonton, both of N.J.

[73] Assignee: American Home Products Corporation, Madison, N.J.

[21] Appl. No.: 380,867

[22] Filed: Jan. 30, 1995

[51] Int. Cl.$^6$ .......................... A61K 31/085; A61K 9/08
[52] U.S. Cl. .................................................. 514/718
[58] Field of Search .............................. 514/718

[56] References Cited

U.S. PATENT DOCUMENTS

| | | | |
|---|---|---|---|
| 3,134,720 | 5/1964 | Green et al. | 167/82 |
| 4,145,440 | 3/1979 | Fitch et al. | 424/287 |
| 4,361,580 | 11/1982 | Peck et al. | 424/287 |
| 4,427,681 | 1/1984 | Munshi | 424/260 |
| 4,453,979 | 6/1984 | De Masi et al. | 106/188 |
| 4,576,645 | 3/1986 | Ravel et al. | 106/25 |
| 4,684,666 | 8/1987 | Haas | 514/557 |
| 4,690,823 | 9/1987 | Lohner et al. | 424/456 |
| 4,788,220 | 11/1988 | Mody et al. | 514/557 |
| 5,028,625 | 7/1991 | Motola et al. | 514/557 |
| 5,141,961 | 8/1992 | Coapman | 514/629 |
| 5,196,436 | 3/1993 | Smith | 514/289 |
| 5,260,073 | 11/1993 | Phipps | 424/465 |
| 5,272,137 | 12/1993 | Blase et al. | 514/54 |
| 5,288,479 | 2/1994 | Gorman et al. | 424/49 |
| 5,338,732 | 8/1994 | Atzinger et al. | 514/178 |
| 5,409,907 | 4/1995 | Blase et al. | 514/54 |

*Primary Examiner*—Shep K. Rose
*Attorney, Agent, or Firm*—John W. Routh; Steven H. Flynn

[57] ABSTRACT

There is provided a taste masked liquid pharmaceutical composition for administration of a relatively large amount of unpleasant tasting medicines. More particularly, the composition comprises a taste masking liquid excipient base for administration of relatively large amounts of unpleasant tasting medicines, said excipient base having higher than normal viscosities due to a combination of a normally solid polyethylene glycol and sodium carboxymethylcellulose.

12 Claims, No Drawings

TASTE MASKING GUAIFENESIN CONTAINING LIQUIDS

CROSS-REFERENCE TO RELATED APPLICATIONS

This application is related to U.S. Ser. No. 08/380,540 filed Jan. 30, 1995 concurrently herewith.

BRIEF DESCRIPTION OF THE INVENTION

The present invention is directed to a taste masked liquid pharmaceutical composition for administration of a relatively large amount of unpleasant tasting medicines. More particularly, the taste masking effect is produced by increasing the viscosity of the liquid excipient base of the composition by adding to the liquid excipient base a viscosity increasing amount of a combination of a normally solid polyethylene glycol and sodium carboxymethyl cellulose.

BACKGROUND OF THE INVENTION

Pharmaceutically acceptable liquid excipient bases for administration of unpleasant tasting medicines are well known in the art. A typical system is described in U.S. Pat. No. 5,260,073 to Roger J. Phipps at column 7 as including a medicine, a solvent, a co-solvent, a buffer, a surfactant, a preservative, a sweetening agent, a flavoring agent, a dye or pigment, a viscosity modifier and water. The patent provides several examples of each ingredient in the system.

Although liquid excipient bases and their many ingredients are well known, unpleasant tasting medicines alone or in combination still present challenges to one skilled in the art to provide better taste masked products and, in certain instances, to provide taste masking for higher dosage amounts of unpleasant tasting medicines in smaller amounts of vehicle.

SUMMARY OF THE INVENTION

According to this invention taste masking of unpleasant tasting pharmaceutical compounds for their administration in relatively large amounts is accomplished by increasing the viscosity of the taste masking liquid excipient base by incorporating therein a combination of a polyethylene glycol and sodium carboxymethyl cellulose. Surprisingly, it has been found that the high viscosity liquid excipient base provides taste masking benefits to the extent that extra strength compositions can be prepared containing increased concentrations of adverse tasting pharmaceutical compositions. For example, guaifenesin, normally administered in dosages of no more than 100 milligrams in 5 milliliters of liquid, may be administered in dosages of 200 milligrams in the same volume of liquid without the patient experiencing an unduly adverse taste.

DETAILED DESCRIPTION OF THE INVENTION

The pharmaceutically acceptable taste masking bases useful in this invention are those having incorporated therein per 100 milliliters of liquid base about 5 to about 20 grams, preferably about 10 to about 15 grams, of polyethylene glycol having an average molecular weight of about 1000 to about 2000, preferably about 1400 to about 1600, and about 0.05 to about 0.6 grams, preferably about 0.1 to about 0.5 grams, of sodium carboxymethyl cellulose, the weight ratio of polyethylene glycol to sodium carboxymethyl cellulose being between about 100:1 and about 20:1, such that the spindle viscosity is between about 150 and about 1000 centipoises at 50 RPM, preferably between about 200 and about 100 centipoises at 50 RPM and more preferably at about 400 to about 700 centipoises at 50 RPM. The base further typically has a spindle viscosity of between about 150 and about 1200 centipoises if measured at 10 RPM. The higher viscosities are preferred for certain applications since such liquids are easier to pour from glass bottles and do not tend to spill from a spoon during administration, especially to children.

The pH of the liquid base is from about 2.5 to about 5. At a lower pH, the sodium carboxymethyl cellulose tends to crystalize out and at a higher pH the taste worsens and more preservatives should be used.

Excipients other than the polyethylene glycol and the sodium carboxymethyl cellulose useful in the practice of the present invention are those known to the art. These include humectants such as glycerin and propylene glycol, preservatives such sodium benzoate and paraben, sweeteners such as sodium saccharin, corn syrup and sorbitol solutions, menthol and various flavoring and coloring agents.

The polyethylene glycols useful in the practice of the present invention are those having an average molecular weight of about 1000 to about 2000. Preferably, the polyethylene glycol has an average molecular weight of about 1400 to about 1600. Most preferably, the polyethylene glycol used in the practice of the present invention has an average molecular weight of about 1450. The use of mixtures of such polyethylene glycols is further within the practice of the present invention. As stated above, the polyethylene glycol component is used in amount of about 5 to about 20 grams, preferably about 10 to about 15 grams, per 100 milliliters of the liquid excipient base.

The polyethylene glycol used in the specific examples was Polyethylene Glycol 1450 N.F. This polyethylene glycol, having a molecular weight of 1450 can be obtained from a number of suppliers. For instance, it is sold by Union Carbide Chemicals and Plastic Company, Inc. of Danbury, Conn. as CARBOWAX® 1450® and by Dow Chemical Company of Midland, Mich. as Dow Polyglycol E1450.

The sodium carboxymethylcellulose used in the specific examples was HERCULES® Cellulose Gum 7MF which is the sodium salt of carboxymethylcellulose with a minimum purity of 99.5%, food grade, with a Type 7 Degree of Substitution and a medium viscosity range of 400–800 cps as a 2% by weight in water solution. The medicines and excipients other than the polyethylene glycol and the sodium carboxymethyl cellulose were of U.S.P. grade.

The pharmaceutical compounds useful for the practice of the present invention include guaifenesin, pseudoephedrine HCl, dextromethorphan and ibuprofen. These compounds are all well known and commercially available.

Guaifenesin may be present in amounts of up to about 300 milligrams per 5 mls. of the excipient base. Preferably, guaifenesin is present in amounts of about 10 to about 300 milligrams per 5 mls. of the excipient base. Most preferably, guaifenesin is present in amounts of about 100 to about 200 milligrams per 5 mls. of the excipient base.

Pseudoephedrine HCl may be present in amount of between about 10 and about 60 milligrams per 5 mls. of the excipient base. Preferably, pseudoephedrine is present in amounts of about 15 to about 30 milligrams per 5 mls. of the excipient base.

Dextromethophan may be present in amounts of between about 5 and about 20 milligrams per 5 mls. of the excipient base. Preferably, dextromethorphan is present in amounts of about 10 to about 15 milligrams per 5 mls. of the excipient base.

Ibuprofen may be present in amounts of from about 50 to about 150 milligrams per 5 mls. of the excipient base. Preferably, ibuprofen is present in amounts of about 50 to about 100 milligrams per 5 mls. of the excipient base.

Although not willing to be bound thereby, it is believed that the polyethylene glycol when melted and mixed with the propylene glycol and the glycerine, serves to solubilize the pharmaceutical compounds and inhibit their crystallization at room temperature. If a normally liquid polyethylene glycol such as PEG 200 or 300 is used, a lesser taste masking effect may result.

The invention will now be described with respect to the following specific examples.

EXAMPLE 1

The formulation of the invention set forth below was prepared in accordance with the following procedure. The example illustrates a formulation containing 200 milligrams of guaifenesin per 5 ml of formulation, double the normal amount, which has an acceptable taste.

| INGREDIENTS | AMT/ 5 ML | % | AMT/ 500 ML |
|---|---|---|---|
| GUAIFENESIN, USP | 200.0 MG | 4.0 | 20.0 g |
| DEXTROMETHORPHAN HBR, USP | 10.0 MG | 0.20 | 1.0 g |
| PSEUDOEPHEDRINE HCl, USP | 30.00 MG | 0.60 | 3.0 g |
| POLYETHYLENE GLYCOL 1450, NF | 500.00 MG | 10.00 | 50.0 g |
| PROPYLENE GLYCOL, USP | 0.75 ML | 15.00 | 75 ml |
| GLYCERIN, USP | 0.25 ML | 5.00 | 25 ml |
| HIGH FRUCTOSE CORN SYRUP 95 | 2.25 ML | 45.00 | 2 25 ml |
| SORBITOL SOLUTION, USP | 0.25 ML | 5.00 | 25 ml |
| l-MENTHOL, USP | 1.20 MG | 0.024 | 0.12 g |
| CITRIC ACID ANHYDROUS, USP | 45.00 MG | 0.90 | 4.5 g |
| SODIUM BENZOATE, USP | 5.00 MG | 0.10 | 0.5 g |
| SACCHARIN SODIUM, USP | 35.00 MG | 0.70 | 3.5 g |
| COLORING AND SWEETENER | 5.15 MG | 0.103 | 0.515 g |
| SODIUM CARBOXY-METHYLCELLULOSE 7MF, USP | 25.00 MG | 0.50 | 2.5 g |
| ART. FRUIT FLAVOR | 0.036 ML | 0.72 | 3.6 ml |
| PURIFIED WATER, USP QS TO | | | 500 ml |

The PEG 1450 was introduced into a flask and melted at 50°–60° C. and 62.5 ml of propylene glycol was added with stirring. The guaifenesin, the dextromethorphan HBr and the pseudoephedrine HCl were then dissolved in the mixture. In a separate flask, the sodium carboxymethylcellulose was dispersed in glycerin, and in a third flask, the sodium benzoate and sodium saccharin were dissolved in 60 ml of purified water. The sodium carboxymethylcellulose dispersion was added to the third flask and stirred for at least 30 minutes or until the preparation becomes thick. The thick preparation was added to the bulk in the first flask. To the first flask were then added the sorbitol solution and the corn syrup with continuous stirring. The menthol was then dissolved in 12.5 ml of propylene glycol and added to the bulk. The citric acid was dissolved in 10 ml water and added to the bulk. The flavors and coloring were added and then purified water to 500 ml.

The resulting formulation has a pH of 3.38, 3.40, a spindle #3 viscosity at 10 RPM of 590 cps and a spindle viscosity at 50 rpm of 534 cps. The ratio of polyethylene glycol to sodium carboxymethylcellulose is 20:1.

The formulation has an acceptable flavor and taste.

EXAMPLE 2

The formulation of this example has the same proportions of medicines and polyethyleneglycol as in the previous example but only one fifth as much sodium carboxymethylcellulose.

| INGREDIENTS | AMT/ 5 ML | % | AMT/1.0 L |
|---|---|---|---|
| GUAIFENESIN, USP | 200.0 MG | 4.0 | 40.0 g |
| DEXTROMETHORPHAN HBR, USP | 10.0 MG | 0.20 | 2.0 g |
| PSEUDOEPHEDRINE HCl, USP | 30.00 MG | 0.60 | 6.0 g |
| POLYETHYLENE GLYCOL 1450, NF | 500.00 MG | 10.00 | 100.0 g |
| PROPYLENE GLYCOL, USP | 0.75 ML | 15.00 | 150.0 ml |
| GLYCERIN, USP | 0.25 ML | 5.00 | 50.0 ml |
| HIGH FRUCTOSE CORN SYRUP 95 | 2.25 ML | 45.00 | 450.0 ml |
| SORBITOL SOLUTION, USP | 0.25 ML | 5.00 | 50.0 ml |
| l-MENTHOL, USP | 1.20 MG | 0.024 | 0.24 g |
| CITRIC ACID ANHYDROUS, USP | 25.00 MG | 0.5 | 5.0 g |
| SODIUM BENZOATE, USP | 7.5 MG | 0.15 | 1.5 g |
| SACCHARIN SODIUM, USP | 35.00 MG | 0.70 | 7.0 g |
| COLORING AND SWEETENER | 5.5 MG | 0.11 | 1.1 g |
| SODIUM CARBOXY-METHYLCELLULOSE 7MF, USP | 5.00 MG | 0.1 | 1.0 g |
| ART. FRUIT FLAVOR | 0.003 ML | 0.06 | 0.6 ml |
| PURIFIED WATER, USP QS TO | | | 1 L |

The procedure for this formulation was essentially the same as in the previous example except that the pseudoephedrine HCl was added with the citric acid dissolved in water and the coloring was separately added dissolved in water.

The resulting formulation has a pH of 3.51, a spindle #1 viscosity at 10 RPM of 236–256 cps and a spindle viscosity of 243–248 cps at 20 RPM. The ratio of polyethylene glycol to sodium carboxymethylcellulose is 100:1.

The formulation has an acceptable taste.

EXAMPLE 3

In this formulation only two medicines, guaifenisin and dextromethorpan HBr were used.

| INGREDIENTS | AMT/ 5 ML | % | AMT/1.0 L |
|---|---|---|---|
| GUAIFENESIN, USP | 200.0 MG | 4.0 | 40.0 g |
| DEXTROMETHORPHAN HBR, USP | 10.0 MG | 0.20 | 2.0 g |
| POLYETHYLENE GLYCOL 1450, NF | 500.00 MG | 10.00 | 100.0 g |
| PROPYLENE GLYCOL, USP | 0.75 ML | 15.00 | 150.0 ml |

-continued

| INGREDIENTS | AMT/ 5 ML | % | AMT/1.0 L |
|---|---|---|---|
| GLYCERIN, USP | 0.25 ML | 5.00 | 50.0 ml |
| HIGH FRUCTOSE CORN SYRUP 95 | 2.25 ML | 45.00 | 450.0 ml |
| SORBITOL SOLUTION, USP | 0.25 ML | 5.00 | 50.0 ml |
| l-MENTHOL, USP | 1.20 ML | 0.024 | 0.24 g |
| CITRIC ACID ANHYDROUS, USP | 30.0 MG | 0.6 | 6.0 g |
| SODIUM BENZOATE, USP | 7.5 MG | 0.15 | 1.5 g |
| SACCHARIN SODIUM, USP | 28.0 MG | 0.56 | 5.6 g |
| COLORING AND SWEETENER | 5.5 MG | 0.11 | 1.1 g |
| SODIUM CARBOXY-METHYLCELLULOSE 7MF, USP | 5.0 MG | 0.1 | 1.0 g |
| ART. FLAVORS | 0.003 ML | 0.06 | 0.6 ml |
| PURIFIED WATER, USP QS TO | | | 1.0 L |

The procedure for this formulation was essentially the same as in Example 2.

The resulting formulation has a pH of 3.45, 3.51, a spindle #1 viscosity at 10 RPM of 177 cps and a spindle viscosity at 20 RPM of 178 cps which rose to 210 cps at both 10 RPM and 20 RPM within 24 hours. The ratio of polyethylene glycol to sodium carboxymethylcellulose is 100:1.

The formulation has an acceptable taste.

EXAMPLE 4

This formulation is similar to Example 2, except that the guaifenesin was 100 milligrams and the PEG content was 350 milligrams and shows that the PEG content must be coordinated with the sodium carboxymethylcellulose content to achieve the proper viscosity.

| INGREDIENTS | AMT/ 5 ML | % | AMT/1.0 L |
|---|---|---|---|
| GUAIFENESIN, USP | 100.0 MG | 2.0 | 200 g |
| DEXTROMETHORPHAN HBR, USP | 10.0 MG | 0.20 | 2.0 g |
| POLYETHYLENE GLYCOL 1450, NF | 350.00 MG | 7.00 | 70.0 g |
| PROPYLENE GLYCOL, USP | 0.75 ML | 15.00 | 150.0 ml |
| GLYCERIN, USP | 0.25 ML | 5.00 | 50.0 ml |
| HIGH FRUCTOSE CORN SYRUP 95 | 2.25 ML | 45.00 | 450.0 ml |
| SORBITOL SOLUTION, USP | 0.25 ML | 5.00 | 50.0 ml |
| l-MENTHOL, USP | 1.20 ML | 0.024 | 0.24 g |
| CITRIC ACID ANHYDROUS, USP | 25 MG | 0.5 | 5.0 g |
| SODIUM BENZOATE, USP | 7.5 MG | 0.15 | 1.5 g |
| SACCHARIN SODIUM, USP | 35.0 MG | 0.7 | 7.0 g |
| COLORING AND SWEETENER | 5.5 MG | 0.11 | 1.1 g |
| SODIUM CARBOXY-METHYLCELLULOSE 7MF, USP | 5.0 MG | 0.1 | 1.0 g |
| ART. FLAVORS | 0.003 ML | 0.06 | 0.6 ml |
| PURIFIED WATER, USP QS TO | | | 1 L |
| PSEUDOEPHEDRINE HCl, USP | 30.0 MG | 0.60 | 6.0 g |

The procedure for this formulation was essentially the same as in the previous example except that the pseudoephedrine HCl was dissolved with citric acid in water.

The resulting formulation has a pH of 3.40, a spindle #1 viscosity at 10 RPM of 101 cps and a spindle #1 viscosity at 20 RPM of 102 cps. The ratio of polyethylene glycol to sodium carboxymethylcellulose is 70:1.

EXAMPLE 5

In this formulation similar to Example 2 only 100 milligrams of guaifenesin was employed, the polyethylene glycol was reduced to 350 milligrams and the sodium carboxymethylcellulose was increased to 12.5 milligrams.

| INGREDIENTS | AMT/ 5 ML | % | AMT/1.0 L |
|---|---|---|---|
| GUAIFENESIN, USP | 100.0 MG | 2.0 | 20.0 g |
| DEXTROMETHORPHAN HBR, USP | 10.0 MG | 0.20 | 2.0 g |
| POLYETHYLENE GLYCOL 1450, NF | 350.00 MG | 7.00 | 70.0 g |
| PROPYLENE GLYCOL, USP | 0.75 ML | 15.00 | 150.0 ml |
| GLYCERIN, USP | 0.25 ML | 5.00 | 50.0 ml |
| HIGH FRUCTOSE CORN SYRUP 95 | 2.25 ML | 45.00 | 450.0 ml |
| SORBITOL SOLUTION, USP | 0.25 ML | 5.00 | 50.0 ml |
| l-MENTHOL, USP | 1.20 MG | 0.024 | 0.24 g |
| CITRIC ACID ANHYDROUS, USP | 25 MG | 0.5 | 5.0 g |
| SODIUM BENZOATE, USP | 7.5 MG | 0.15 | 1.5 g |
| SACCHARIN SODIUM, USP | 35.0 MG | 0.7 | 7.0 g |
| COLORING AND SWEETENER | 5.5 MG | 0.11 | 1.1 g |
| SODIUM CARBOXY-METHYLCELLULOSE 7MF, USP | 12.5 MG | 0.25 | 2.5 g |
| ART. FLAVORS | 0.003 | 0.06 | 0.6 ml |
| PURIFIED WATER, USP QS TO | | | 1 L |
| PSEUDOEPHEDRINE HCl, USP | 30.00 MG | 0.60 | 6.0 g |

The procedure for this formulation was essentially the same as Example 4.

The resulting formulation has a pH of 3.49, a spindle #1 viscosity at 10 RPM of 176 cps and a spindle viscosity at 20 RPM of 174 cps. The ratio of polyethylene glycol to sodium carboxymethylcellulose is 28:1.

The formulation has an acceptable taste.

EXAMPLE 6

In this experiment, the amount of guaifenesin was increased to 200 milligrams per 5 milliters and the amount of the other ingredients remained the same as in Example 5. The pH of the resulting formulation was 3.63 and the spindle #1 viscosity is 363 cps at 10 RPM and 357 cps at 20 RPM. The taste of the formulation is acceptable.

EXAMPLE 7

In this formulation similar to Example 3 only 100 milligrams of guaifenisin were employed, the polyethylene glycol was reduced to 350 milligrams and the sodium carboxymethylcellulose was increased to 12.5 milligrams.

| INGREDIENTS | AMT/ 5 ML | % | AMT/1.0 L |
|---|---|---|---|
| GUAIFENESIN, USP | 100 MG | 2.0 | 20.0 g |
| DEXTROMETHORPHAN HBR, USP | 10.0 MG | 0.2 | 2.0 g |
| POLYETHYLENE GLYCOL 1450, NF | 350 MG | 7.0 | 70.0 g |
| PROPYLENE GLYCOL, USP | 0.75 ML | 15.00 | 150.0 ml |
| GLYCERIN, USP | 0.25 ML | 5.00 | 50.0 ml |
| HIGH FRUCTOSE CORN SYRUP 95 | 2.25 ML | 45.00 | 450 ml |
| SORBITOL SOLUTION, USP | 0.25 ML | 5.00 | 50 ml |
| l-MENTHOL, USP | 1.20 ML | 0.024 | 0.24 g |
| CITRIC ACID ANHYDROUS, USP | 30.0 MG | 0.6 | 6.0 g |
| SODIUM BENZOATE, USP | 7.5 MG | 0.15 | 1.5 g |
| SACCHARIN SODIUM, USP | 28.0 MG | 0.56 | 5.6 g |
| COLORING AND SWEETENER | 5.5 MG | 0.11 | 1.1 g |
| SODIUM CARBOXY- METHYLCELLULOSE 7MF, USP | 12.5 MG | 0.25 | 2.5 g |
| FLAVORS | 0.003 ML | 0.06 | 0.6 ml |
| PURIFIED WATER, USP QS TO | | | 1 L |

The procedure for this formulation was essentially the same as in Example 3.

The resulting formulation has a pH of 3.45, a spindle #1 viscosity at 10 RPM of 202 cps and a spindle viscosity at 20 RPM of 197 cps. The ratio of polyethylene glycol to sodium carboxymethylcellulose is 28:1.

The formulation has an acceptable taste.

We claim:

1. A taste masked, liquid pharmaceutical composition comprising guaifenesin and a liquid excipient base consisting essentially of water and per 100 milliliters of said base (i) about 5 to about 20 grams of polyethylene glycol having a molecular weight of about 1000 to about 2000, and (ii) about 0.05 to about 0.6 grams of sodium carboxymethyl cellulose, the weight ratio of said polyethylene glycol to said sodium carboxymethyl cellulose being between about 100:1 and about 20:1, the pH of the excipient base being between about 2.5 and about 5 and the spindle viscosity being between about 150 and about 1000 centipoises at 50 RPM, said guaifenesin being dissolved in the liquid excipient base.

2. The composition of claim 1 wherein the guaifenesin is present in an amount of between about 100 and about 300 milligrams per 5 milliliters of the excipient base.

3. The composition of claim 2 wherein the guaifenesin is present in an amount of about 200 milligrams per 5 milliliters of the excipient base.

4. A taste masked, liquid pharmaceutical composition comprising guaifenesin and a liquid excipient base consisting essentially of per 100 milliliters of said base (i) about 5 to about 20 grams of polyethylene glycol having a molecular weight of about 1000 to about 2000, (ii) about 0.05 to about 0.6 grams of sodium carboxymethyl cellulose, (iii) about 10 to about 30 ml of propylene glycol, (iv) about 2 to about 10 ml of glycerine, (v) about 25 to about 60 ml of corn syrup, (vi) about 2 to about 10 ml of sorbitol solution, and (vii) about 15 to about 35 ml water, the weight ratio of polyethylene glycol to sodium carboxymethyl cellulose being between about 100:1 and about 20:1, the pH being between about 2.5 and about 5 and the spindle viscosity being between about 200 and about 1000 centipoises at 50 RPM, said quaifenesin being dissolved in the liquid excipient base.

5. The composition of claim 4 wherein the guaifenesin is present in an amount of between about 100 and about 300 milligrams per 5 milliliters of the excipient base.

6. The composition of claim 5 wherein the guaifenesin is present in an amount of about 200 milligrams per 5 milliliters of the excipient base.

7. A taste masked, liquid pharmaceutical composition which is easy to pour yet does not tend to spill from a spoon during administration comprising guaifenesin and a liquid excipient base consisting essentially of per 100 milliliters of said base (i) about 10 to about 15 grams of polyethylene glycol having a molecular weight of about 1400 to about 1600, (ii) about 0.1 to about 0.5 grams of sodium carboxymethylcellulose, (iii) about 12 to about 20 milliliters of propylene glycol, (iv) about 4 to about 6 milliliters of glycerine, (v) about 40 to about 50 milliliters of corn syrup, (vi) about 3 to about 7 milliliters of sorbitol solution, and (vii) about 15 to about 25 milliliters of water, the weight ratio of polyethylene glycol to sodium carboxymethylcellulose being between about 100:1 and about 20:1, the pH being between about 3 and about 4 and the spindle viscosity being between about 400 and about 700 centipoises at 50 RPM, said guaifenesin being dissolved in the liquid excipient base.

8. The composition of claim 7 wherein the guaifenesin is present in an amount of about 100 to about 300 milligrams per 5 milliliters of the excipient base.

9. The composition of claim 8 wherein the guaifenesin is present in an amount of about 200 milligrams per 5 milliliters of the excipient base.

10. A method of taste-masking unpleasant tasting guaifenesin comprising incorporating guaifenesin in a liquid excipient base consisting essentially of water and, per 100 milliliters of said base, (i) about 5 to about 20 grams of polyethylene glycol having a molecular weight of about 1000 to about 2000, and (ii) about 0.05 to about 0.6 grams of sodium carboxymethylcellulose, the weight ratio of said polyethylene glycol to said sodium carboxymethyl cellulose being between about 100:1 and about 20:1, the pH of said base being between 2.5 and about 5 and the spindle viscosity being between about 150 and about 1000 centipoises at 50 RPM, said guaifenesin being dissolved in the liquid excipient base.

11. The method of claim 10 wherein the guaifenesin is present in an amount of between about 100 and about 300 milligrams per 5 milliliters of the excipient base.

12. The method of claim 11 wherein the guaifenesin is present in an amount of about 200 milligrams per 5 milliliters of the excipient base.

* * * * *